United States Patent [19]
Hansen et al.

[11] Patent Number: 5,939,021
[45] Date of Patent: Aug. 17, 1999

[54] HOMOGENEOUS BINDING ASSAY

[76] Inventors: W. Peter Hansen; Petra B. Krauledat, both of 121 Top of Deane Hill Rd., P.O. Box 315, Canaan, N.Y. 12029

[21] Appl. No.: 08/789,211

[22] Filed: Jan. 23, 1997

[51] Int. Cl.⁶ ............... G01N 21/00; G01N 33/543; C12M 1/00; A01N 1/02
[52] U.S. Cl. ............... 422/55; 422/50; 422/55; 422/41; 422/82.05; 422/82.09; 436/518; 436/501; 436/525; 436/527; 436/805; 436/808; 435/283.1; 435/6; 435/287.2; 435/975
[58] Field of Search ............... 435/6, 283.1, 287.2, 435/975; 436/501, 518, 525, 527, 805, 808; 422/50, 55, 41, 82.05, 82.09

[56] References Cited

FOREIGN PATENT DOCUMENTS

98/04740  2/1998  WIPO .

OTHER PUBLICATIONS

Stookey et al., "Full–color photosensitive glass" (1978) J. Appl. Phys. vol. 49 No. 10 pp. 5114–5123.
Skillman, et al., "Effect of Particle Shape on the Spectral Absorption of colloidal silver in Gelatin" (1968) The Journal of Chemical Physics, vol. 48, No. 7, pp. 3297–3304.
Bohren et al., "Surface Modes in Small Particles" (1983) Absorption and Scattering of Light by Small Particles pp. 325–381.
Laserna, et al., "Effect of Substrate Optical Absorption on Surface–Enhanced Raman Spectrometry on Colloidal Silver" (1992) Analytical Chemistry, vol. 64, No. 17, pp. 2006–2009.
Kaplan, et al., "Interferences in chemical analysis" (1989) Clinical Chemistry Theory, analysis and correlation 2nd Ed., pp. 808–819.
Bohren et al., "Particles Small Compared with the Wavelength" (1983)Absorption and Scattering of Light by Small Particles pp. 130–157.
Mirkin et al., "A DNA–based method for rationally assembling nanoparticles into macroscopic materials," *Nature*, vol. 382, pp. 607–609, Aug. 15, 1996.
Mirkin et al., "DNA–Induced Assembly of Gold Nanoparticles—A Method for Rationally Organizing Colloidal Particles into Ordered Macroscopic Materials," *Abstracts of Papers of the American Chemical Society*, vol. 212, P249–INOR, Aug. 25, 1996.
Heath et al., (Direct Absorption Spectroscopy Experiments on Carbon and Metal Clusters, *Abstacts of Papers of the American Chemical Society*, vol. 198, P22–PHYS, Sep. 10, 1989.
Mirkin et al., "DNA–Based Strategies for Rationally Organizing Nanoparticles into Functional Macroscopic Materials: New Ultrasensitive Colorimetric Detection Methods for DNA," *Abstracts of Papers of the American Chemical Society*, vol. 214, P17–MTLS, Sep. 7, 1997.
Alivisatos et al., "Organization of 'noncrystal molecules' using DNA," *Nature*, vol. 382, pp. 609–611, Aug. 15, 1996.
Robert Service, "DNA Ventures into the World of Designer Materials," *Science*, vol. 277, pp. 1036–1037 (Aug. 22, 1997).
Elghanian et al., "Selective Colorimetric Detection of Polynucleotides Based on the Distance–Dependent Optical Properties of Gold Nanoparticles," *Science*, vol. 277, pp. 1078–1081 (Aug. 22, 1997).

*Primary Examiner*—James C. Housel
*Assistant Examiner*—Pensee T. Do
*Attorney, Agent, or Firm*—Graham & James LLP

[57] ABSTRACT

A homogeneous method of measuring chemical binding relies on resonant, or "amplified," optical extinction (light scattering plus absorption) from a defined, specific class of colloidal particles wherein the real term n of the complex refractive index n–ik approaches zero while the imaginary term k approaches $\sqrt{2}$. Chemical binding partners are coated onto the particles, which either aggregate or disperse during the binding reaction, causing an optical extinction change at one wavelength that is quantitatively related to the number of single colloidal particles and another at a second wavelength that is quantitatively related to the number of doublet colloidal particles. The method employs: (1) a specific class of colloidal particles that exhibit optical resonance and that are substantially smaller in diameter than a wavelength of visible light; (2) a one-step process of colloidal particle aggregation; and (3) a photometric extinction measurement at wavelengths where the particles exhibit optical resonance.

24 Claims, 8 Drawing Sheets

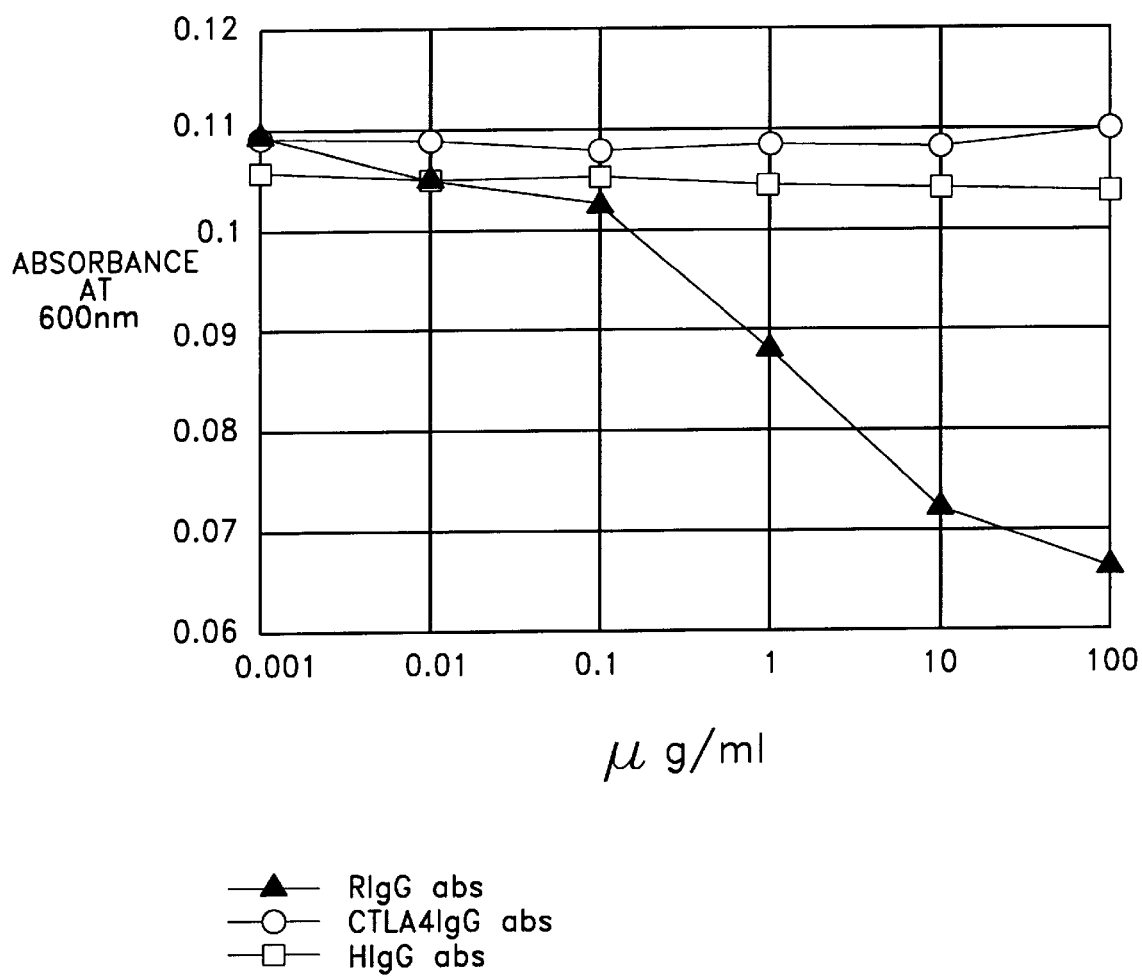

HOMOGENEOUS BINDING ASSAY

BACKGROUND OF THE INVENTION

1. Field of the Invention

The present invention relates to the spectroscopy of colloidal particles that are used to advantage in monitoring chemical binding assays. The invention pertains to colloids that are much smaller than a wavelength of light and show the phenomena of resonance at certain wavelengths which: (1) enhances optical absorbance above the background of liquid samples; and (2) introduces a strong particle shape dependence into the optical absorbance spectrum.

2. Description of Related Art

Chemical binding assays have been used in the laboratory for a wide range of analyses including the detection of genetic material, ligand-receptor interactions for therapeutic drug screening, and immunoassays for tumor markers, hormones, and infectious disease detection. The basis of a chemical binding assay is the existence of highly specific chemical binding between two molecular components. Such binding events can involve two or more complex macromolecules such as a protein ligand and its receptor, an adhesion molecule and its target binding molecule, or two polynucleotides, or can involve interaction between a complex molecule such as an antibody or lectin with a smaller molecule known as a hapten. The important point is a "lock in key" fit between the two components that results in a relatively high affinity of one component for the other.

The typical strategy of a chemical binding assay is to use one component of a binding pair to assay for the presence and concentration of the second component of the pair. Most commonly one of the components of the pair is immobilized on a solid substrate so that it can be readily separated from the other material used in the analysis. That is, a sample solution containing an unknown quantity of the second component of the binding pair is added to the immobilized first component so that the two can bind together. Then the immobilized component (and the bound second component) is removed from the sample solution, washed to remove impurities, and then assayed for the presence of the unknown second component. This process is known as a bound-free separation It should be appreciated that while chemical binding is often explained in terms of a "binding pair," the actual situation is frequently more complex. Although any particular chemical binding occurs between two components, when assaying an unknown macromolecule by means of a chemical binding assay, more than two different components may easily be involved. For example, assume that the unknown material is a protein "antigen" produced by a disease organism. A good way of identifying the protein antigen is by binding a specific antibody to the antigen. The antibody is a special protein with a specific binding site that is complementary to a specific site or epitope on the protein antigen. The point is that most proteins are large enough to contain more than one epitope. If the unknown material is a bacterium or a virus, there may be hundreds or thousands of epitopes. This is to say, although an antibody is highly specific to the antigen or virus, many different antibodies may be specific to different sites on the antigen or virus. Therefore, the strategy of the chemical binding assay may advantageously involve more than one pair of chemical binding components. For example, two or more antibodies specific to different epitopes on a macromolecule or cellular component can be used in a single chemical binding assay. In the case of an assay designed to detect a specific nucleic acid sequence, multiple binding components, each specific to a different subsequence, can advantageously be used.

In many laboratory analyses that depend on chemical binding assays, the test is automated so that little human participation is required. This necessarily requires more or less complex fluid handling equipment which, in addition to dispensing accurate and precise fluid volumes, must also perform the separation of the immobilized component from the sample solution, the bound-free separation. Bound-free separation is generally cumbersome, and requires specialized equipment such as centrifuges or microplate washers.

In order to eliminate the bound-free separation step and reduce the time and equipment needed for a chemical binding assay, so-called "homogeneous assay" methods have been developed. Many of these methods still immobilize one component of the binding pair, but manage to detect the presence of the second component of the binding pair without a bound-free separation. Examples of homogeneous, optical methods are the EMIT method of Syva, Inc. (Sunnyvale, Calif.), which operates through detection of fluorescence quenching, the laser nephelometry latex particle agglutination method of Behringwerke (Marburg, Germany), which operates by detecting changes in light scatter, the LPIA latex particle agglutination method of Mitsubishi Chemical Industries, the TDX fluorescence depolarization method of Abbott Laboratories (Abbott Park, Ill.), and the fluorescence energy transfer method of Cis Bio International (Paris, France).

Of the optically based, homogeneous methods, those that involve particle aggregation have been preferred for general use because there is no limitation as to analyte size or molecular weight. In the TDX method of fluorescence depolarization, the analyte molecular weight must be low (e.g. hapten analyses) the assay operates by detecting differences in molecular rotation between a small free analyte and that same analyte bound to a comparatively large binding member. In the EMIT system there is a steric chemical limitation on the ability of analytes to cause detectable fluorescence quenching—excessively large analytes are unable to effect quenching. Particle binding assays do not have these inherent molecular weight limitations, and have been used for analyses with molecular weights ranging from a few hundred Daltons to a few million Daltons.

Opposing the molecular weight advantage, optically monitored, particle binding assays have a well-known restriction which relates to nonspecific chemical binding. That is, the aggregation of large particles (e.g. of the order of one micrometer in diameter) is easily detected by changes in optical extinction, but these particles present large surface areas that are prone to nonspecific chemical binding. Nonspecifically bound material can cause false readings and generally decreases the accuracy of the analysis. The relation between particle size and nonspecific binding can be appreciated from the following examples. A one-micrometer particle, such as is used in many visually read particle aggregation chemical binding assays, presents a surface area that has room for a nonspecifically bound monolayer of several thousand macromolecules, approximately. The LPIA optical extinction method utilizes polystyrene (latex) particles with diameters slightly less than the wavelength of visible light, i.e., 250 nanometers. These particles have the capacity to nonspecifically bind only several hundred macromolecules. If particles are further reduced in size to be far smaller than a wavelength of visible light, say approximately 20 nanometers to 50 nanometers, the particles will have room for only one to ten nonspecifically bound macromolecules. With larger particles, opportunity for nonspecific binding to particles, and nonspecific cross-linking between particles, is clearly great. Unfortunately, when the particles are much smaller than a wavelength of light, the optical signals produced by these particles are usually greatly reduced.

It is known that metal colloids may at time produce strongly colored solutions; see "Full-color photosensitive glass," Stookey, S. D., Beal, G. H. and J. E. Pierson, *J Appl. Phys.* 49: 5114–23 (1978). Leuvering et al. (U.S. Pat. No. 4,313,734) discloses that metallic colloidal particles can be used in protein binding assays with detection representing a color change. This reference advocates the use of a wide range of metals and metal oxides. Further, this reference advocates the use of a mixed colloid with particles of a variety of sizes and many doublet and other aggregate particles.

In one example using silver, Leuvering et al. demonstrates the use of a gray-yellow-green colloidal suspension with multiple, complex, bound A gray-yellow-green colloidal silver suspension is indicative of a mixture of small (approximately 10 nm diameter), single particles (yellow color) and large, preformed, particle aggregates up to diameters of approximately 130 nm (gray-green color) (see *Absorption and Scattering of Light by Small Particles,* Bohren, C. F. and Huffman, D. R., p.372, John Wiley and Sons, New York, 1983).

Laserna et al. ("Effect of Substrate Optical Absorption on Surface-Enhanced Raman Spectrometry on Colloidal Silver," Laserna, J. J., Cabalin, L. M., and Montes, R., *Anal. Chem.* 64:2006–09 (1992)), has described methods of making aggregate free, colloidal silver suspensions, and has stressed that a single absorption peak at approximately 400 nm (which yields a pure yellow color) is indicative of a highly monomeric suspension, and that broad absorption bands at longer wavelengths between 450 nm and 900 nm are indicative of aggregates even when these bands are not the region of maximum absorption.

Thus, the potential advantage of less nonspecific binding with very small particles is at least partly lost by the presence of much larger particles and aggregates in the assay of Leuvering et al. Further, this assay method appears to be largely a heterogeneous assay that depends on bound-free separations. Until the present invention it has not been possible to greatly reduce nonspecific binding through the use of extremely small particles because the small particles produced optical signals that were greatly diminished as compared to larger particles. These optical signals were generally inadequate for use in homogeneous assays where the sample solution is not removed by washing so that other substances present in the sample solution produce confounding background signals.

OBJECTS AND SUMMARY OF THE INVENTION

It is an object of the present invention to provide chemical binding assays based on particles much smaller than a wavelength of visible light so that nonspecific binding can be greatly reduced;

It is a further object of the present invention to provide an easily automated homogeneous chemical binding assay; and It is yet another object of the present invention to provide a sensitive chemical binding assay that allows binding kinetic measurements and concentration determination by means of simple optical extinction.

These and other objects are met in a homogeneous method of measuring chemical binding that relies on resonant, or "amplified," optical extinction (light scattering plus absorption) from a defined, specific class of colloidal particles wherein the real part n of the complex refractive index n–ik approaches zero while the imaginary term k approaches $\sqrt{2}$. Chemical binding partners are coated onto the particles, which either aggregate or disperse during the binding reaction, causing an optical extinction change at one wavelength that is quantitatively related to the number of single colloidal particles and another at a second wavelength that is quantitatively related to the number of doublet colloidal particles. The method employs: (1) a specific class of usually metallic, colloidal particles that exhibit optical resonance and that are substantially smaller in diameter than a wavelength of visible light; (2) a one-step process of colloidal particle aggregation; and (3) a photometric extinction measurement at wavelengths where the particles exhibit optical resonance.

It is demonstrated that when small particles are fabricated from the class of optically resonant materials, the extinction in a first, unique wavelength band is greatly amplified over that achieved with small particles not belonging to this class of materials. Such amplification is useful when using small particles because small particles are to be preferred over large particles in chemical binding measurements in order to reduce surface area, and the accompanying interferences from nonspecific chemical binding.

It is further demonstrated that extinction changes in this first wavelength band during chemical binding quantify the number of singlet particles. It is also shown that extinction in a second wavelength band quantifies the number of particle dimers and/or aggregates. The extinction changes in the two wavelength bands are of opposing sign and can be followed in real time to establish a reaction rate and correct for unknown, time invariant background extinction.

The invention is particularly useful in the field of biochemical binding assays, such as genetic material (polynucleotide) assays, ligand-receptor assays, and immunoassays; where initially spherical particles can be biochemically sensitized to form dimers and higher order aggregates when a specific target substance is present. The invention is equally useful in assays where the inhibition of binding by a specific substance is measured.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 7 shows the reaction shown in FIG. 6 measured at 600 nanometers (dimer resonance).

DETAILED DESCRIPTION OF THE PREFERRED EMBODIMENTS

Figure 1A:
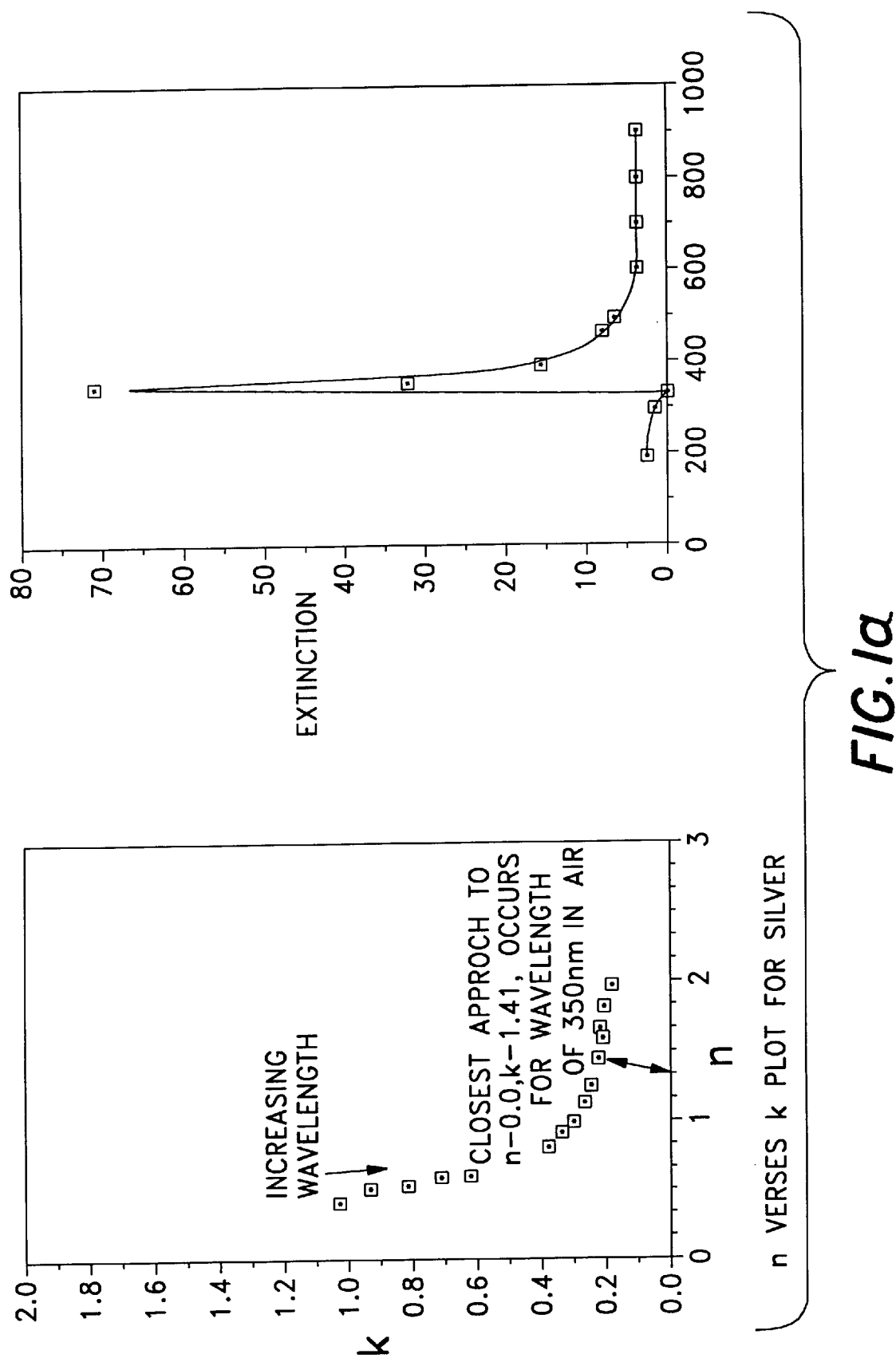
FIG. 1a shows a parametric plot traced in an n–k plane for a material having a resonant wavelength.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a homogeneous chemical binding assay based on colloidal particles that show resonant wavelengths that greatly increase the sensitivity of optical extinction measurements.

The present invention deals with an improved homogeneous chemical binding assay that uses an optical detection method. Specifically, as will be detailed below, the method operates by monitoring chemical binding events as a change in optical extinction at specific wavelengths. In many measurements of optical extinction in solutions, changes in extinction are caused solely by a change in absorption of light by chemicals in the solution. This is frequently expressed as optical absorbance, which has the property of being directly related to chemical concentration. However, in the case of many chemical binding assays, including the present invention, particles are employed so changes in optical extinction are often due to changes in light scatter, as well as changes in absorbance as the particles change aggregation state due to the chemical binding reaction.

In the case of particles that do not strongly interact with (absorb) visible light (i.e., latex or plastic particles), changes in light scatter accounts for the majority of any change in optical extinction. For example, weakly absorbing particles that are smaller than a wavelength of light will have very little effect on optical transmission. If these same particles aggregate to approach or exceed, in diameter, a wavelength of light, significant light may be scattered by the aggregate depending on the refractive index, n of the particles, as compared to the refractive index of the suspending medium (usually an aqueous solution).

However, in the case of particles made from materials that strongly absorb light, other, more complex interactions are possible. These materials, such as metals, strongly interact with light so as to be virtually opaque (i.e., strongly absorbing). In this case, there is the additional possibility that light will be reflected (back scattered), as well as side scattered and absorbed. While light scatter by transparent particles is largely governed by refractive index, scatter (reflectivity) by strongly absorbing particles is governed by absorbance as well as by index of refraction. For such particles the more commonly used index of refraction, n, must be replaced by the complex index of refraction, n–ik, where k is known as the "imaginary" portion or the absorption index and n is known as the "real" portion of the index. The real portion of the complex index of refraction details the speed of light in the material. For example, in a substance where n=1.5, the speed of light is two thirds that of the speed in a vacuum (i.e., 1/11.5=0.66667). The imaginary portion of the complex index of refraction is directly related to the absorption coefficient α for light absorption at wavelength λ in the material according to following equation:

$$\alpha = \frac{4\pi\kappa}{\lambda}$$

The absorption coefficient relates intensity of light incident, $I_{incident}$, on a medium of thickness t to the intensity of light exiting the medium:

$$I_{exit} = I_{incident} \cdot e^{-\alpha t}$$

The origin of the complex refractive index in metals is the motion of substantially free electrons in response to the oscillating electric field of incident light. For some metals, this motion is frequency dependent so that the complex index of refraction varies with the wavelength of incident light, as indicated by writing both n and k as functions of wavelength (λ), i.e. n(λ) and k (λ).

When these materials with high absorbance are made into particles, there are some unexpected effects on optical transmission. An excellent source of information about these phenomena is to be found in *Absorption and Scattering of Light by Small Particles*, Bohren, C. F. and Huffman, D. R., John Wiley & Sons, New York, 1983 (hereafter Bohren & Huffman, incorporated herein by reference). First, it is possible for particles significantly smaller than a wavelength of light to exhibit very strong effects on optical extinction (Bohren & Huffman, page 341). Second, shape of the particle can have an unexpectedly large effect on optical extinction and on the wavelength maxima of such extinction. Bohrens & Huffman have reviewed experimental and theoretical work that has been carried out on the shape dependence of light scatter and absorption by small particles (particles smaller than a wavelength of light) (pages 342–357) in both the visible and infrared regions of the electromagnetic spectrum. These authors point out that the dependence of light scattering and absorption on particle shape is difficult to treat in closed form, and they draw attention to specific, simplified cases where solids of revolution, such as ellipsoids, have been analyzed.

Bohren & Huffman treat the case where a spherical particle is deformed mathematically into a prolate ellipsoid and analyze the changes that occur in light scattering and absorption. In particular, they treat the case where the real part of the refractive index of a spherical particle, n, approaches zero and the imaginary part of the refractive index, k, approaches √2. Under these conditions, the spherical particle is optically resonant at a specific wavelength, $\lambda_R$, and exhibits light scatter and absorption cross-sections at that wavelength that are well above the Rayleigh scattering level (this enhanced optical extinction is also called "amplification" in the lexicon of the present invention). When the resonant particle is deformed into a prolate ellipsoid (ellipsoid of revolution around the major axis), the original resonant wavelength splits into two resonances, one at a shorter wavelength (blue-shifted) and one at a longer wavelength (red-shifted). Evidence for this resonant split has also been found by Skillman and Berry, who created ellipsoidal silver particles in a photographic process (Effect of Particle Shape on the Spectral Absorption of Colloidal Silver in Gelatin, Skillman, D.C. and Berry, C. R., *J. of Chem. Phys.*, 48:3297–104 (1968)), and by Stookey et al. (Full-color Photosensitive Glass, Stookey, S. D., Beall. G. H. and Pierson, J. E. *J. Appl. Phys.* 49:5114–23 (1978)) who studied the effects of particle shape on color of glass containing the particles.

Optical resonances that occur in bulk solids can become significantly accentuated if the solid is reduced to particle form with a diameter substantially less than a wavelength of light. Unusually strong extinction (absorbance and light scatter) spectra maxima are created by single, substantially spherical colloidal particles (i.e., particles substantially smaller in diameter than a wavelength of light). However, these same resonances are less significant for particles that are larger—that approach a wavelength of light in diameter. These colloidal particles are termed "resonant" or "amplifying" to denote that they scatter and absorb light in narrow wavelength bands substantially above the usual inverse fourth power of wavelength light scatter (Rayleigh scattering) and the inverse first power absorption for particles of colloidal size. The resonant maximum becomes advantageously narrower, while the spectral width of the resonant maximum becomes advantageously greater and the shape dependence for the resonance becomes advantageously greater the more closely the above conditions for n and k are met.

The single, shape-dependent resonance maximum for strongly resonant, spherical colloidal particles splits into two maxima when the spherical particle is topologically deformed into a prolate ellipsoidal particle with an aspect of ratio (major axis to minor axis) greater than 1:1. One maximum is shifted slightly towards shorter wavelengths ("blue-shifted"), and is generally not well-differentiated from the original, single resonance maximum. The second maximum is shifted more markedly toward the longer wavelengths ("red-shifted") and is broader and generally more readily differentiated from the original resonance maximum. The two split resonances move farther apart in terms of wavelength as the aspect ratio of the ellipsoid increases.

It is a very important aspect of the present invention that the inventors have found a similar resonant splitting occurring in spherical particles when two such particles are coupled by a chemical binding pair to form a dimer made up of two spheres so long as the resonant conditions n and k of the particle material are satisfied. One might anticipate that bringing two spherical resonant particles into close proximity would not show the same effect as actual particle deformation, especially when the particles are actually separated by a layer of the chemical binding components that have very different, nonresonant, refractive indices from that of the particles. For example, in the present invention particles with a diameter of 50 $\mu$m are typically given a protein coat about 15 $\mu$m thick. To this protein coat are attached antibodies having a length of about 7.5 $\mu$m. When two particles are brought together by antibody mediated binding, the particle surfaces are separated by about 45 $\mu$m—a distance practically equal to the particle diameter !. That resonant splitting would occur even when the two spherical particles are not in intimate contact, but are instead separated by a chemical surface coating layer, such as a layer of protein, is a phenomena completely unanticipated by Bohrens & Huffman and all other workers in this field. It should be emphasized that resonant splitting due to chemical binding dimerization does not occur for nonresonant or weakly resonant particles.

It will readily be appreciated that this unexpected discovery that resonant splitting occurs even in the presence of layers of chemical binding components can be put to tremendous use in chemical binding assays. Up until now optical detection of chemical binding was dependent on heterogeneous bound-free separations or upon very special fluorescence or polarization techniques discussed above. It had been known that highly absorptive particles like metal particles might be used in chemical binding assays, but there was no sensitive or reproducible way to quantitate the chemical binding process in a homogeneous assay. With the present discovery it is possible to use simple optical extinction to measure the formation of particle dimers (through the appearance of increased extinction at the split resonant wavelength) and the concomitant disappearance of the singlet particles (through the decrease of extinction at the original resonant wavelength). In the present invention the optical extinction decreases in a wavelength band bracketing the original resonant wavelength of the spherical singlet particles with the optical extinction increasing in wavelength bands bracketing the split resonant wavelengths. The primary requirement is that the assay employ particles of an "amplified" or resonant material. Furthermore, it is essential that the particles be almost entirely singlet particles so that the dimerization change is not swamped out. In addition, the particles must be significantly smaller than a wavelength of light so that the resonance effects are not overcome by more ordinary light scatter effects.

Figure 1B:
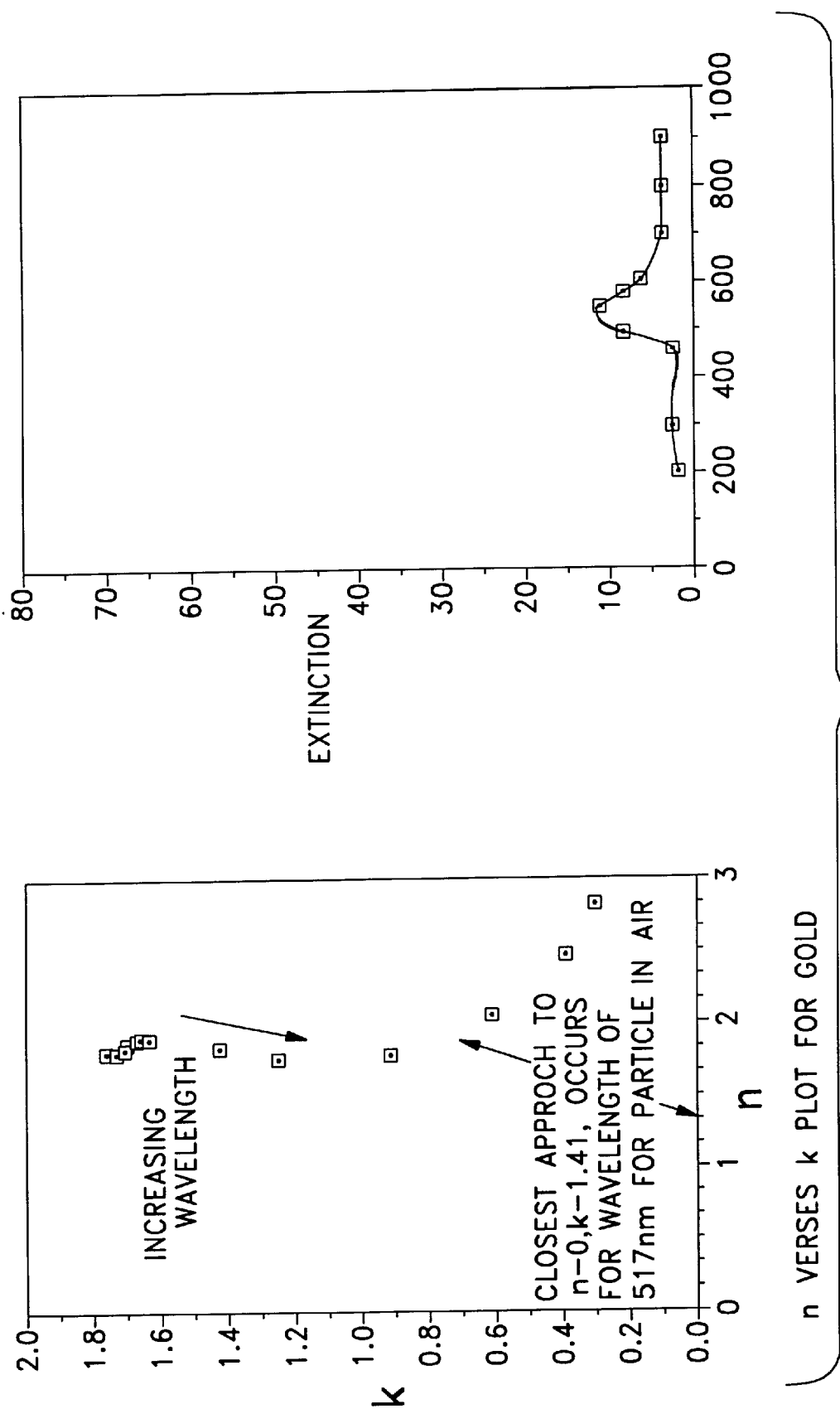
FIG. 1b shows a parametric plot traced in an n–k plane for a material having no significant resonant wavelength.

The class of materials suitable for the present invention are those for which the real part n of the refractive index approaches zero and the imaginary part of the refractive index, k approaches $\sqrt{2}$ at one or more wavelengths, $\lambda_R$. Such wavelengths are termed "resonant wavelengths" or "resonances" for the purposes of this invention. There is a distinct extinction spectrum maximum at the resonant wavelength for single, substantially spherical, colloidal particles that are composed of material fulfilling the above requirements. FIG. 1 illustrates parametric curves, traced in n and k planes with wavelength, $\lambda$, as the parameter. FIG. 1a shows a substance with a resonant wavelength while FIG. 1b shows a material having no significant resonant wavelength.

Figure 2:
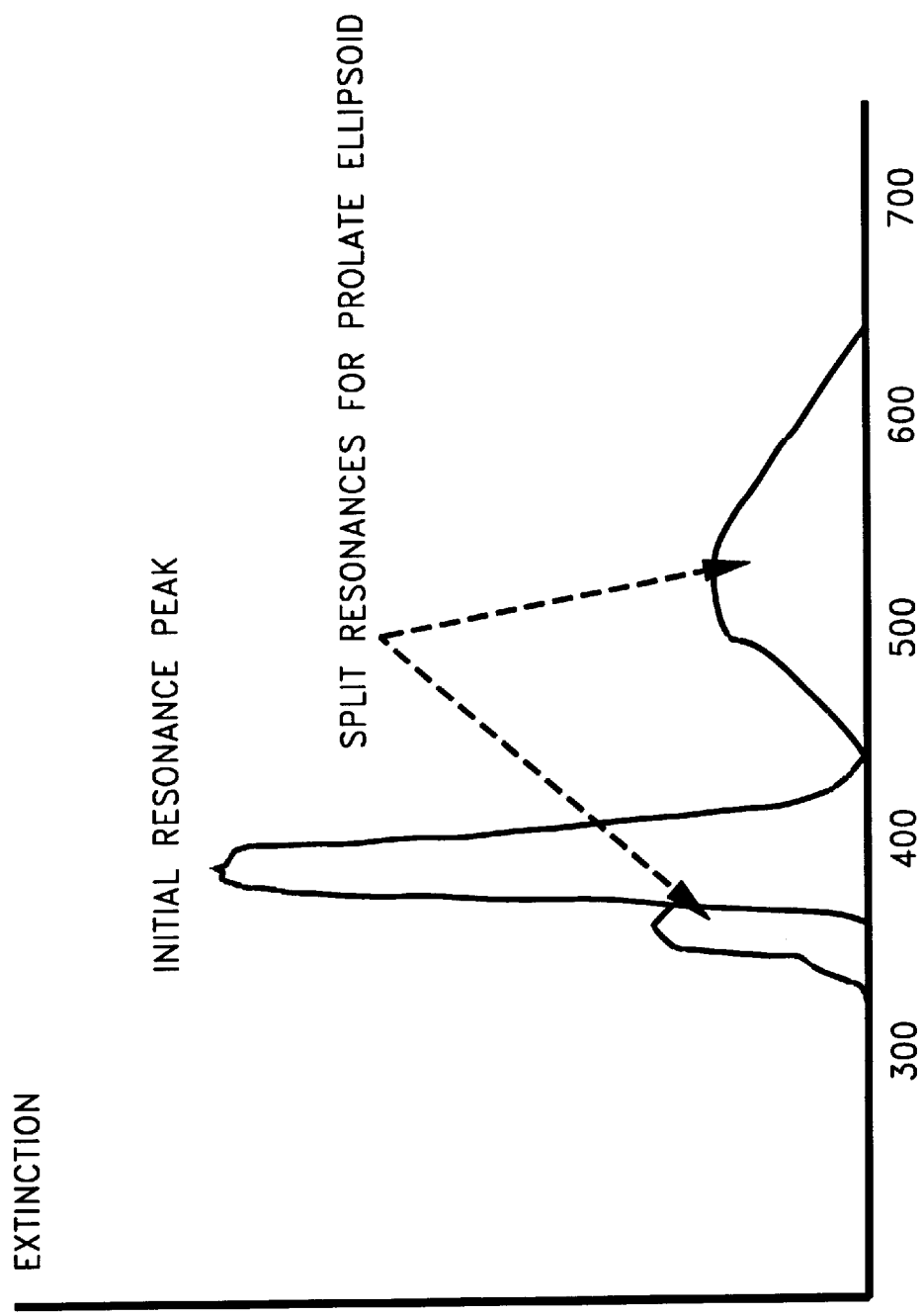
FIG. 2 shows calculated resonant splitting of prolate particles.
Figure 3:
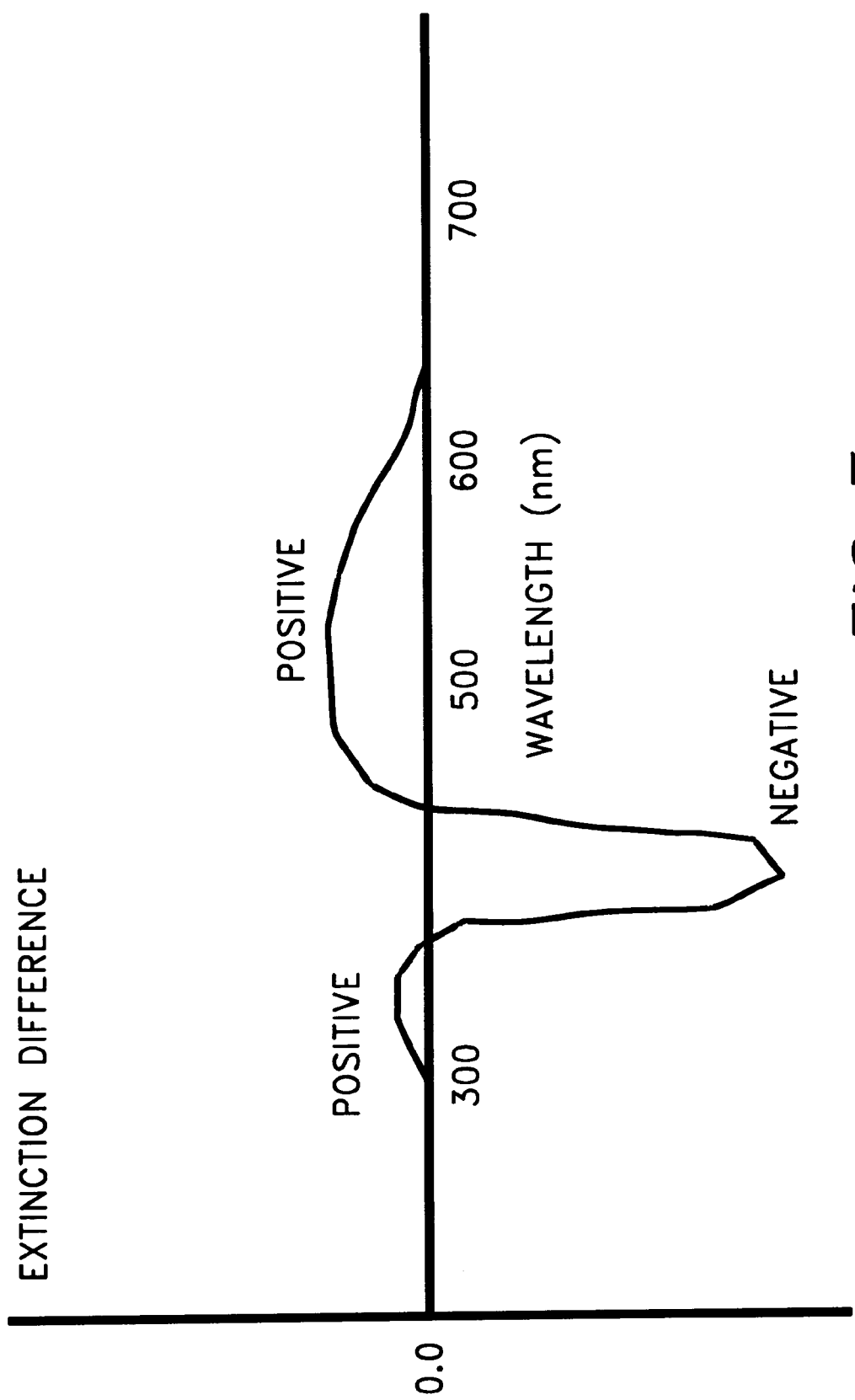
FIG. 3 shows a difference spectrum of the prolate particles of FIG. 2.

FIG. 2 illustrates the calculated extinction resonance split that occurs when a resonant, spherical particle becomes elongate, such as occurs when they are deformed into prolate ellipsoids. FIG. 3 represents the calculated "difference spectrum" for a solution of resonant, monomeric metal particles that has been partially converted into prolate ellipsoids of 2:1 aspect ratio. The absorbance difference is negative (indicating a decrease) under the initial resonant peak (singlet spherical particles) and positive (indicating an increase) under the two split resonances (deformed particles).

In order to practice this invention with substantially "aqueous" solutions, it is necessary that the resonant wavelength for the colloidal material lie in a region of the optical spectrum where water is sufficiently transparent to enable an extinction (absorbance and light scatter) measurement to be made. When a one centimeter, perpendicular, optical path length through the measurement solution is used for an extinction determination, the conventional boundaries for this spectral region are approximately 250 nanometers to 1000 nanometers. Water becomes increasingly opaque to light with wavelengths shorter than 250 nanometers or longer than 1000 nanometers wavelength.

The inventors have discovered that chemical binding-mediated dimerization not only causes resonant splitting, but the resonant splitting occurs even when the resulting "particle" shape is not strictly ellipsoidal (actual shape is two spheres separated by a protein-filled gap), as taught by Bohrens & Huffman for actual particles. Multilayered metallic coatings of different metals can produce a shift generally in the direction of the resonant wavelength of the metal exhibiting the strongest resonance. For example, spherical colloidal gold shows a very weak resonance between approximately 520 nanometers and 550 nanometers (depending on the exact size of the particle). This resonance is not, by itself, adequately strong for practicing the present invention; however, after successive coatings of silver are applied, the resonance grows in strength and shifts toward the 380 nanometer resonant wavelength of silver, approaching this latter value asymptotically as the silver thickness is increased.

Significantly, the present inventors have found that resonant splitting can be used to simultaneously distinguish between singlet particles and dimers in a particle agglutination, chemical binding reaction in a simple optical cuvette. The optical distinction between singlets and dimers by resonant splitting is used to obtain both a high sensitivity and a wide assay range. Dimers can be monitored at the red-shifted wavelength at an early stage of the reaction in order to gain high sensitivity, and singlets can be measured at the original resonance wavelength in order to obtain a wide assay range. It is to be noted that extinction (light scatter and absorption) at the singlet resonant wavelength decreases monotonically toward a final equilibrium value as aggregation proceeds through all stages, but extinction at the red-shifted or blue-shifted resonances for dimers, at first increases as dimers are initially formed, then decreases to an equilibrium level as aggregation proceeds toward equilibrium as dimers are converted into higher aggregates that do not show strong resonances.

The increase in the dimer resonances is highly sensitive, but limited in range. The decrease in the singlet resonance is less sensitive, but it extends over a much wider range. Both resonances can be monitored simultaneously in the same cuvette using equipment that is highly compatible with commercial spectrophotometers. The present invention uses a shape dependence rather than a size dependence in light scattering and absorption by small, optically resonant particles to solve the problem of achieving high sensitivity and wide range in particle agglutination assays. These parameters can be readily measured by a visible light spectrophotometer. To create an automated assay based on the present invention all that is needed is automated or manual fluidic handling to add a measured aliquot of sample to a measured aliquot of prepared detection reagent (resonant colloidal particles coated with at least one member of a chemical binding pair), mix the result and place it into a spectrophotometer cuvette for analysis. It is possible to provide the detection reagent in a disposable cuvette as a container so that the sample can be directly added to the measuring cuvette. The analyses can be further simplified by equipping the containers of the detection reagent with bar codes or other coding means to automatically indicate the required analysis parameters (i.e., resonant wavelengths, detection reagent specificity and kinetic values, etc.).

The present invention requires materials that have resonant wavelengths as described above. Another consideration in evaluating materials for use as colloidal particles in the present invention is the spectral position of the red-shifted and blue-shifted split resonances that occur after initially spherical, resonant particles bind to form elongated complexes such as dimeric pairs. For example spherical aluminum colloids have an initial resonance at 190 nanometers wavelength, which, unfortunately, is not in a spectral region where water is transparent. When aluminum dimers form, the red-shifted split resonance are calculated to be in the region of the optical spectrum beyond 250 nanometers where water is transparent. Thus, the red-shifted split resonance can allow the present invention to use resonant wavelengths that normally would not be in the wavelength range required to penetrate water.

It is necessary that at least one of the resonances, either the initial spherical particle resonance or one of the split resonances, be measurable above the background of absorbance or light scatter of the measurement solution. For example, when human serum samples are used, then there is a "background" absorbance that is caused by nonresonant, small particle light scatter (Rayleigh scatter) and by direct optical absorption by serum components such as proteins. Nonresonant, small particle light scatter and optical absorption is most intense at ultraviolet wavelengths. It is an important aspect of this invention to use colloidal particles that satisfy the resonant conditions of n and k as closely as possible, in order to elevate the resonant extinction well above the nonresonant background extinction of the sample. It will be appreciated that this is primarily a problem in homogeneous binding assays. Where there is a bound-free separation step, as in heterogeneous assays, the interfering serum components are removed before the assay results are read optically.

The pure, elemental metallic substances that satisfy the above criterion for having a resonant wavelength, or one or more shifted, split resonant wavelengths, in a spectral region where water is substantially transparent and that are also predicted (i.e., strong resonant wavelength) to be measurable above a background of approximately 20% human serum are aluminum, magnesium, potassium, and silver. Composite substances, such as silver coated on gold particles, also are predicted to be suitable for the present invention.

Aluminum particles in the small size range suitable for the present invention are difficult to make without an oxide layer. An oxide layer is detrimental to the aluminum resonance, and without further improvements in current particle-making technology, aluminum would seem to be impractical for use the present invention. Unfortunately, neither magnesium nor potassium are chemically compatible with water and are, hence, unsuitable for use in the present invention unless some type of protective surface modification can be developed.

Silver meets all of the necessary criteria for this invention, as does silver coated onto gold to form a composite particle. As such, these two materials are the best known to the inventors at the present time. Persons skilled in the art of the optical properties of materials will recognize that other metallic elements, compounds and/or alloys thereof, as well as certain semiconductor elements, compounds, and/or alloys thereof could meet the necessary optical criteria for this invention; especially the criterion that the real part of the refractive index, n, approach zero and the imaginary part of the refractive index, k, approach the square root of two ($\sqrt{2}$). With these guidelines, further, suitable materials may be identified and fall within the claims of the present invention.

Of particular applicability to the present invention are semiconductor material (i.e., gallium arsenide, germanium, silicon and similar compounds) known as "quantum wells." The electron excitation bands and gaps of these materials are so arranged that they produce strong optical resonance signals. Unfortunately, these resonant wavelengths are generally located in the infra-red portion of the spectrum where water is not transparent. However, it has been discovered that when these materials are fabricated as small particles, generally within the dimensions preferred for the present invention, the gap between the excitation bands is widened. A widened gap will absorb only a photon of a higher energy level, i.e., one within the visible spectrum. ("Size Effects In The Excited Electron States Of Small Colloidal CdS Crystallites," Rossetti, R., Ellison, J. L., Gibson, J. M. and Brus, L. E., *J. Chem. Phys.*, 80:4464–69 (1984)). These quantum well particles are known as "quantum dots" or "Q dots" and are presently of importance in microelectronics where they used in solid state and not in liquid solutions.

There are four primary ways in which strong optical extinction resonances (light scatter and absorption resonances) in singlet spherical, colloidal (i.e., with a diameter substantially less than a wavelength of visible light) particles are used in the present invention. First, strong optical extinction resonances in spherical, colloids can be used to increase the concentration of sample in the final reaction mixture to gain assay sensitivity. With nonresonant particles, one is forced to use low serum concentrations (generally in the range of 1% to 5%) in the final spectrophotometric measurement solution because the background of higher serum concentration would completely overwhelm the optical signals from the chemical binding reaction. This adversely affects the assay's sensitivity—the lowest concentration at which the analyte concentration can be measured. Resonant extinction permits the use of approximately a factor of ten increase serum concentrations (10% to 50%) for concomitantly improved analyte detection sensitivity without a bound-free separation.

Second, strong optical extinction resonances in spherical colloids allows one to reduce the diameter of the particle which, in turn, enhances thermal motion, increases the rate of reaction, and limits the particle surface area available for nonspecific binding. With nonresonant particles, the particle diameter must be greater, near or above the wavelength of visible light, so that there will be sufficient interaction with light waves so as to be detected above the sample background. As a general guideline for small particles (diameters much less than a wavelength) absorption dominates over scattering, which means that the extinction increases approximately as the volume of the particle (cube of the diameter) (Bohrens & Huffman, page 136). Thus, a material with a strong resonant wavelength, such as that for silver at 420 nanometers, the optical extinction is approximately 10 times that for the strongest wavelength of nonresonant material, i.e., gold at ~550 nanometers. Therefore, one requires a silver particle of only about one-half the diameter and, therefore, only one-fourth the surface area to be seen at the same extinction level as gold above equal serum backgrounds. The four-fold decrease in surface area offered by silver lowers the risk of nonspecific interferences with the analyte-specific binding reaction by four-fold, and the two-fold decrease in particle diameter increases the diffusion coefficient of the particle by two-fold and, hence, the binding reaction rate by two-fold. A comparison with polystyrene particles that are commonly used in particle agglutination immunoassays, and are completely nonresonant, favors silver even more strongly, since these particles absorb light only poorly.

Third, strong optical extinction resonances in spherical colloidal particles permits lowering of the concentration of particles, thereby enhancing the detection sensitivity for the analyte. From the standpoint of order-of-magnitude calculations, the number of active binding sites on the particles per milliliter should be approximately 10 to 100 times greater than the desired analyte measurement sensitivity expressed in molecules per milliliter. Under these conditions, the assay will be approximately optimized for sensitivity and range of analyte concentration. By way of example, consider an immunoassay using two antibodies that bind to two separate epitopes on a give antigen. The first antibody is bound to a first suspension of silver particles and the second antibody is bound to a second suspension of silver particles. When both suspensions are mixed with the antigen, pairs of silver particles will be brought together by "sandwiching" the target antigen between a particle of the first suspension and a particle of the second suspension, and resonant splitting will occur. If one assumes that the concentration of the target antigen is $1\times10_{-13}$ M, this translates to a molecular concentration for the target of $6\times10^7$ molecules per milliliter and, according to the above rule, a silver particle concentration of approximately $1\times10^9$ particles per milliliter. With nonresonant particles such as colloidal gold, this particle concentration cannot be detected above a serum background. With resonant particles, such as silver, this particle concentration can be detected above 1% to 50% serum samples, especially by monitoring the red-shifted resonance which occurs in a spectral region where serum-related Rayleigh light scattering is low. Thus, the red-shifted resonance provides a measure of silver particle dimers, which is the main aggregate form that should be created in this hybridization example.

Fourth, strong optical extinction resonances in spherical colloids creates an optical signal that is strongly shape dependent. This strong shape dependence provides a means to simultaneously monitor the formation of particle dimers, which enables high sensitivity detection of low concentrations of analyte molecules and to also monitor the decrease in singlet particles, which enables detection of a broad range of analyte molecule concentrations without the need to serially dilute samples with high analyte concentration. This provides a novel, dichromatic means to simultaneously monitor the formation of particle dimers and also monitor the decrease in singlet particles by separately measuring the original resonance peak and the red-shifted resonance peak with a grating spectrophotometer, filter photometer, or light scatter photometer. Extinction from particles that are "off resonance" or nonresonant are weakly shape dependent and cannot be used in this mode.

In performing a homogeneous silver particle assay, one can also monitor the kinetic rate of binding, which permits a one-step simplified assay including the necessary correction for endogenous color in the sample. Endogenous color in the sample occurs in human or animal serum samples that have undergone hemolysis or in urine samples with highly variable color, and in the testing of therapeutic drug compounds where the compounds are variably colored. Kinetic methods for background correction have been described by Kaplan and Pesce (Kaplan, L. A. and Pesce, A. J., "Clinical Chemistry, Second Edition," The C. V. Moseby Company, St. Louis, 1989, page 815).

Substantially spherical, singlet colloidal particles can be coated with specific chemical binding substances (surface coating) that can cause a linking between pairs, or multiples of particles. This linking is either promoted or inhibited when a specific chemical substance (analyte) is present in a liquid sample. Linking can be caused by a number of chemical binding events such as the interaction between antigens and antibodies, the hybridization of complementary strands of polynucleotides, or the binding between ligands and receptors. More specifically, one particle can be coated with a first antibody that binds to a first site on an analyte, and the other particle can be coated with a second antibody that binds to a second site on the same analyte. With this configuration particles are linked by the analyte which is "sandwiched" between the first and second antibodies. In another specific embodiment one particle can be coated with a polynucleotide and the other particle coated with another polynucleotide, where both polynucleotides are complementary to adjacent sequences on a third, target polynucleotide. When these three polynucleotides are hybridized, the two particles become linked in close proximity to one another. In yet another specific embodiment, a receptor is bound to one particle and a ligand to that receptor is bound on the other particle. When free ligand, or an effective antagonist of receptor-ligand binding, is present, particle linking is inhibited. Such ligand-receptor methods can be readily extended to include secondary binding events.

PREFERRED MODE OF OPERATION OF INVENTION

The following examples are described for the case of silver colloids, being the best mode known at the present time. While the present invention is not limited to immunoassay, examples are drawn primarily from this field.

In the present invention, spherical silver particles that are about five to ten-fold smaller than an optical wavelength are used (i.e., about 20–50 nanometers in diameter). This generally assures that only the lowest order, so called "surface mode" resonance, and not higher order resonances, will be excited. It is the lowest order surface mode resonance that is affected by the composite shape of the bound particles and is used advantageously in the present invention. Spherical particle diameters less than approximately 150 nanometers meet this criterion for visible light.

Colloidal silver particles with relatively narrow size distributions of approximately 10% coefficient of variation about the mean, and with mean sizes ranging from 10 nanometers to 50 nanometers were obtained from a commercial source (Goldmark Biological of Phillipsburg, N.J., U.S.A., and British Biocell International of Cardiff, Wales, U.K.). Electron microscopy revealed that the particles thus prepared were spherical according to the definition used to describe this invention. The suspensions thus obtained were yellow and not gray-yellow-green, which was indicative of a very low level of preformed aggregates. Dynamic light scatter analysis confirmed less than 1% preformed aggregates. Table 1 shows the results of the analysis. The vast majority of the particles are singlets of between 26 and 35 nanometers in diameter. A small population of doublets exists at around 80 nanometers. This technique measures hydrodynamic radius rather than direct particle size so that the doublets appear to be more than twice the size of the singlets. What is important is that the mixture is almost entirely singlets so that the dimer resonant single is very small before chemical binding occurs.

TABLE 1

| Size (nm) | % | Size (nm) | % | Size (nm) | % |
|---|---|---|---|---|---|
| 15.8 | 0.0 | 35.1 | 5.9 | 78.2 | 0.3 |
| 17.4 | 0.0 | 38.8 | 0.0 | 86.4 | 0.2 |
| 19.2 | 0.0 | 42.9 | 0.0 | 95.5 | 0.1 |
| 21.3 | 0.0 | 47.4 | 0.0 | 105.5 | 0.0 |
| 23.5 | 0.0 | 52.4 | 0.0 | 116.6 | 0.0 |
| 26.0 | 29.1 | 57.9 | 0.0 | 128.9 | 0.0 |
| 28.7 | 35.3 | 64.0 | 0.0 | 142.5 | 0.0 |
| 31.7 | 29.0 | 70.7 | 0.0 | 157.5 | 0.0 |

Resonant particles were coated with bovine serum albumin (BSA) in one instance and with goat anti-rabbit polyclonal antibodies in another instance by typical adsorption techniques. As a general rule, the protein coating step is performed at or near the isoelectric point of the protein. However, for the heterogeneous protein preparations such as the polyclonal antibodies an alkaline pH is employed. Specifically, 1.0 M Tris-HCl buffer, pH 9.0 was added to the silver colloid suspension to final concentration of 20 mM Tris buffer to adjust the pH of the silver colloid. Approximately 100 µg/ml antibody was preadjusted to pH 9.0 by dialysis against a 20 mM Tris-HCl buffer, pH 9.0. Antibodies were added to the silver colloid suspension to a final concentration of 10 µg/ml. The suspension was gently stirred for 10 minutes. Ten percent BSA, pH 9.0 was added to a final concentration of 1% BSA. After 20 minutes, the silver conjugate was centrifuged for 10 minutes at 14,000×g. The colloid pellet was resuspended in 20 mM Tris-HCl, pH 8.2 with 1% BSA. This procedure was used for the goat anti-rabbit polyclonal antibodies. As a general rule, depending on the adsorption characteristics of the protein, the protein is titrated at between 1 and 15 µg/ml to determine the best coating concentration.

EXPERIMENT 1

Figure 4:
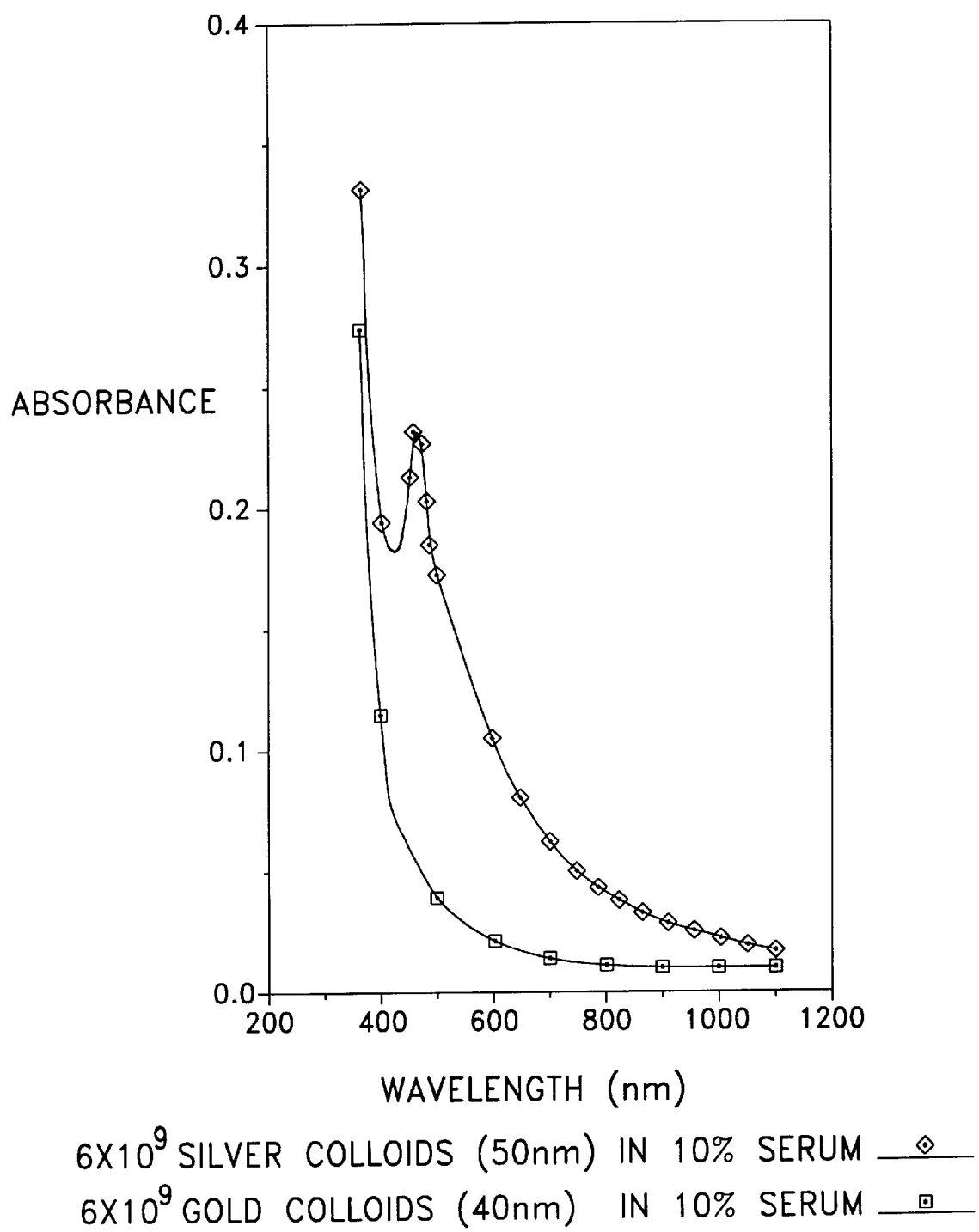
FIG. 4 shows the optical extinction of antibody-coated silver (resonant) particles as compared to similarly prepared gold (nonresonant) particles.

Goat, anti-rabbit, antibody-coated, and BSA post-coated silver particles with 50 nanometer mean diameter were suspended in serum at a particle concentration of approximately $6 \times 10^9$ particles per milliliter with a final serum concentration of 10%. FIG. 4 shows that when optical measurements were made, a resonant peak 10 was clearly discernible above the serum background. By comparison, gold colloids of the same size and concentration could not be discerned above the same 10% serum background. At a serum concentration of 50%, the silver colloid peak was still distinguishable from the background (data not shown).

EXPERIMENT 2

Figure 5:
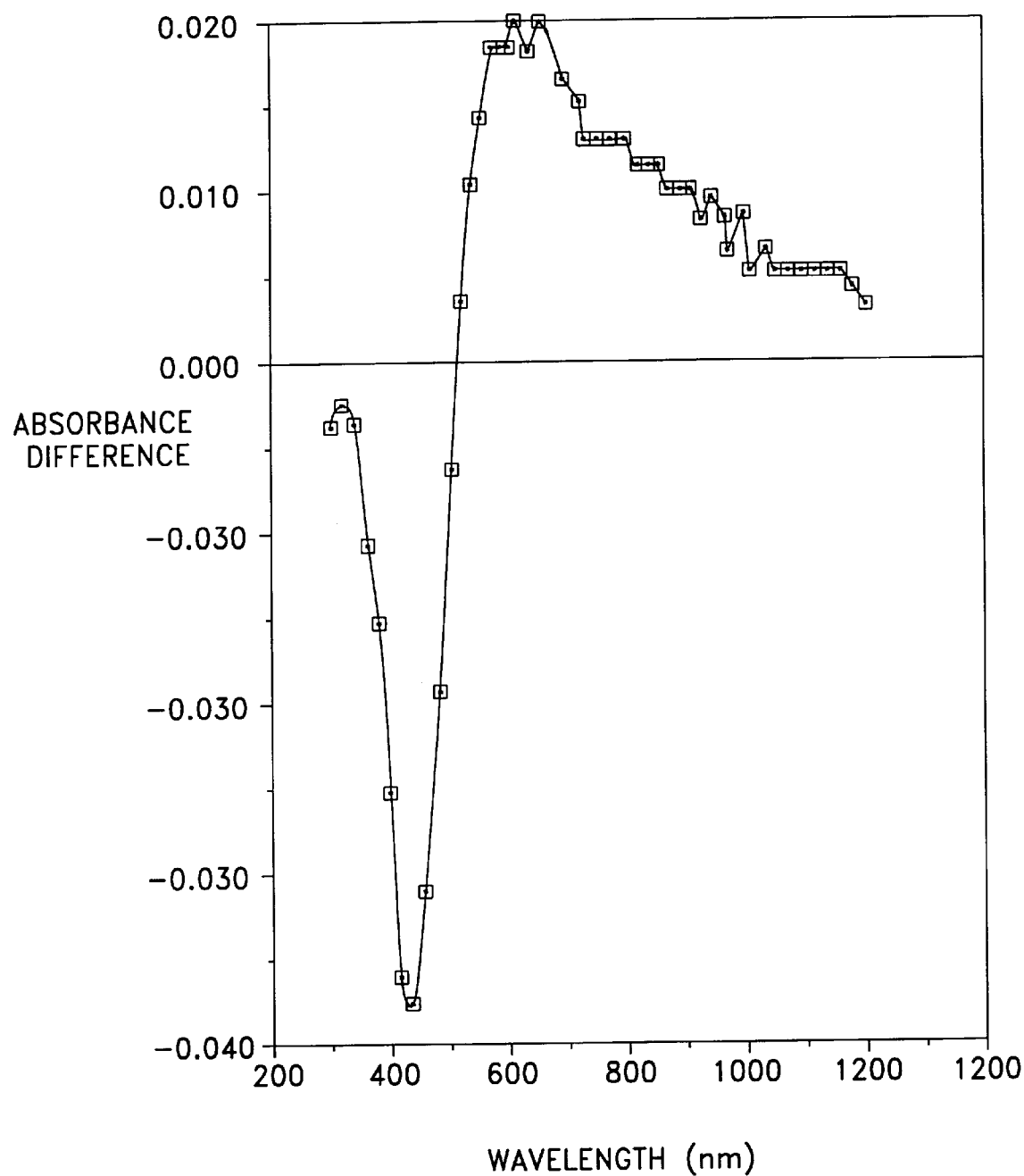
FIG. 5 shows a difference spectrum representing changes in resonant wavelengths as silver particles are bound together by antibodies.

BSA coated silver particles of 50 nanometer diameter were combined with an aqueous solution of anti-BSA antibodies in neutral phosphate buffer, and allowed to aggregate (bind) over time at room temperature in a one centimeter path cuvette. Despite the nonmetallic gap between two linked particles that is produced by the BSA coat and the linking antibody, the silver resonance spectrum showed a decreased extinction at 420 nanometers and an increased extinction in the red region as predicted by the split resonance model for elongate shapes. The short wavelength shifted split resonance is not well-resolved from the main resonance, because, unlike the long wavelength shifted split resonance, the short wavelength shift is small. The complete difference spectrum for this reaction is shown in FIG. 5.

EXPERIMENT 3

Figure 6:
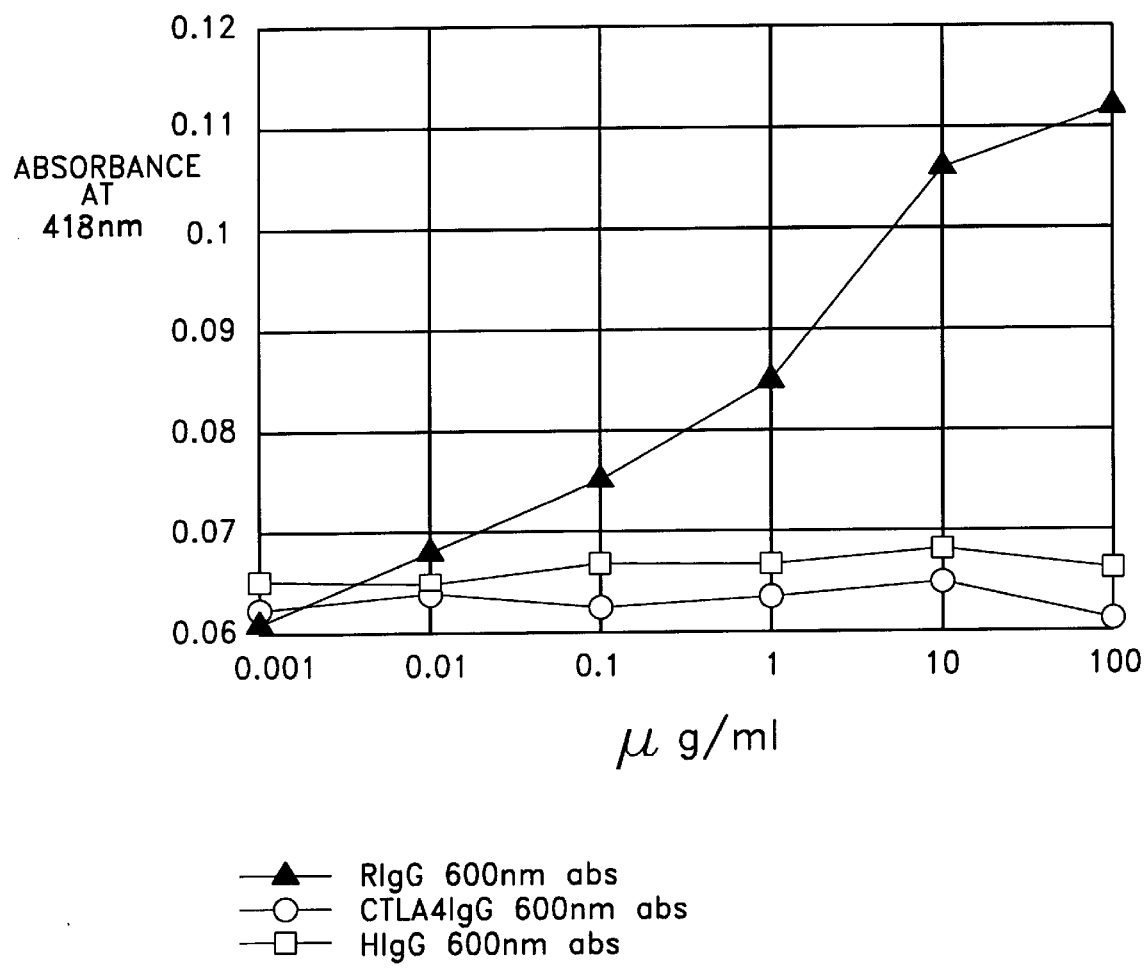
FIG. 6 shows a binding reaction measured at 418 nanometers (singlet resonance)

The same type of particles as used in Experiment 1 were suspended in a 1 cm path length cuvette with rabbit immunoglobulin (IgG) acting as the second member of the binding pair. The rabbit IgG formed a bridge between particles by becoming bound by the goat anti-rabbit IgG bound to the particles Initially dimers are formed but as the incubation proceeds, higher order multimers form. After 15 min of reaction, dose-response measurements were made at 418 nm (singlet resonance) as shown in FIG. 6 and at 600 nm (dimer resonance) as shown in FIG. 7. For a given dose (i.e., a given rabbit IgG concentration), the response at 418 nm was a decrease in absorbance corresponding to a decrease in the number of resonant singlet particles, and the response at 600 nm was seen to be an increase in absorbance corresponding to an increase in the number of resonant dimer.

When similar reactions are allowed to proceed up to about 1 hr, the singlet resonance continues to decrease, but the dimer resonance ends and begins, instead, to decrease, indicating the formation of higher order aggregates that deplete the dimer population and do not show a strong resonance signal. As the dose of rabbit IgG is increased from a very low, but detectable, level of 10 picoM, both optical responses followed a sigmoidal curve that can be used in conjunction with control reactions to define the useful range of the assay. Two control reactions are shown in FIGS. 6 and 7 using, in one instance, a genetically engineered protein and the other using human IgG to replace the rabbit IgG. These control reactions produced a substantially flat response over the range of the concentrations shown. At 418 nm the specific reaction could be distinguished from either control reaction over a 1,000-fold range of analyte concentrations before reaching a plateau. The assay range may depend on the specific binding pairs so this data is offered by way of example only.

EXPERIMENT 4

Polynucleotides can be assayed in much the same way as antibodies. In a first step the silver particles are coated with polynucleotide binding proteins using the methods described above for antibodies. The silver particles can be coated either with avidin (a biotin-binding protein isolated from egg whites) or with anti-biotin antibodies. Biotinylated DNA probes can be readily purchased or prepared by standard procedures. Alternatively, any other nucleic acid binding technique such as the use of anti-digoxigenin antibodies can be employed, in which case the polynucleotide probes must be accordingly labeled.

As mentioned above, the binding strategy is to prepare biotinylated probes complementary to two different polynucleotide sequences of the analyte polynucleotide. The required methods are well-known to one of ordinary skill in the art of Molecular Biology. Separate probes are made from two adjacent polynucleotide sequences both of which are complementary to a target gene sequence (the analyte). These probes are then immobilized on separate populations of silver colloidal particles. When hybridization to the target sequence occurs, two silver particles will be brought close together by the "bridging" target gene, and resonant splitting will occur. The optical extinction changes at 420 nanometers and 600 nanometers are indicative of this binding and can be used to estimate the concentration of the analyte polynucleotide. Further, this process can be monitored kinetically and under different binding (stringency) conditions to obtain additional information about the analyte polynucleotide. Because of steric hindrance it is virtually impossible to have more than two particle simultaneously bind to a analyte polynucleotide. Therefore, the dimer signal will increase to a maximum and without an ultimate decrease due to multimer formation.

EXPERIMENT 5

The inhibition of binding or a receptor to its ligand can also be readily assayed with the present invention. This is of particular utility in testing diverse collections of chemical compounds to discover agents with potential therapeutic applications as receptor antagonists (i.e., drug screening). For example, a preparation of silver colloidal particle is first coated, employing the methods detailed above, with a readily commercially available monoclonal antibody to BSA to act as a model for a "receptor." A second population of silver particles is separately coated with BSA to represent a "ligand." Additional benefits may be achieved by titrating the actual number of these protein ligands bound to the surface of the silver particle to a minimal amount which may be readily determined empirically. In this example, ovalbumin or another non-reactive protein may be subsequently used to complete the protein coating of the colloidal particles so that non-specific binding is reduced. Minimizing the quantity of either or both the "ligand" and "receptor" molecules is not essential for the purpose of drug screening but can have the beneficial effect of increasing the formation of dimeric particles (as opposed to multimeric particles) and, thereby, increase the absorbance at the shifted resonant wavelength.

Equal concentrations, i.e., $6 \times 10^9$ particles/ml, of both the "receptor" and "ligand" particles are combined to form a final suspension and time is allowed for binding to come to equilibrium. At this point the maximal number of colloidal particles will be present as dimers or higher oligomeric forms. This suspension can now be used to test for inhibitors of the receptor-ligand interaction. As a representative example, soluble BSA can be added at increasing concentrations. This addition results in a dose dependent increase in absorbance at or near 420 nm. If the system has been optimized for the formation of dimeric particles as described above, there will also be a concomitant decrease at the longer wavelength which is characteristic of the dimeric species.

It will be appreciated by those skilled in the art that small molecule inhibitors or receptor-ligand binding may be identified by this approach. Such inhibitors or receptor antagonists may be useful as therapeutic drugs for a variety of human clinical applications. Identification of receptor antagonists may generally be accomplished by first coating one population of particles with a receptor of interest and a second population with its cognate ligand. After mixing and equilibration, a large number of aliquots of an appropriate size can be introduced into cuvettes or wells of a microtiter plate. Candidate compounds or pools thereof can then be taken from a large, diverse chemical library and individually added to each of the wells. Absorbance determinations are made at appropriate time points and active compounds are identified as those which produce a specific increase in absorbance at the wavelength characteristic of the monomeric silver particle, i.e., 420 nm. Depending on the conditions under which the colloidal suspensions are prepared, inhibitory compounds may, in addition, produce a decrease in absorbance at the wavelengths characteristic of dimeric particles. Monitoring changes at dual wavelengths may have particular utility in eliminating "false positives" which might through random interference (absorbance) from colored compounds.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A system for optical detection of chemical binding in a homogeneous format without any bound-free separation, the system comprising:

spectrophotometric optical detection means for determination of optical extinction in a liquid sample at at least one predefined wavelength;

a detection reagent comprising:

colloidal particles in an aqueous solution, said particles formed from a material selected to have a complex refractive index n−ik wherein a real part n of the index approaches zero when an imaginary part k approaches $\sqrt{2}$, thereby yielding a resonant optical extinction suitable for detection by the spectrophotometric optical detection means with said particles being spherical single particles having diameters smaller than a wavelength of visible light, and first members of a first chemical binding pair attached to surfaces of said particles, wherein the system detects particle-particle association related to binding of a second member of said chemical binding pair to the particle-attached first member;

means to mix a sample to be analyzed with the detection reagent to form a sample/detection reagent mixture; and means to present the sample/detection reagent mixture, without performing a bound-free separation, to said optical detection means for conducting analysis wherein extinction changes at the predefined wavelength are indicative of changes in particle-particle association due to presence within the sample of a substance that alters, positively or negatively, binding of the second member to the first member of the chemical binding pair.

2. The system of claim 1, wherein the spectrophotometric optical detection means determines the optical extinction at a wavelength where water is substantially transparent to light.

3. The system of claim 1, wherein said material is a semiconductor quantum well material and said particles are quantum dots.

4. The system of claim 1, wherein said material is metal.

5. The system of claim 4, the metal is selected from the group consisting of silver and gold coated with silver.

6. The system of claim 1, wherein the extinction change at the predefined wavelength is proportional to the number of single colloidal particles in the sample/detection reagent mixture.

7. The system of claim 1, wherein the extinction change at the predefined wavelength is proportional to the number of doublet colloidal particles in the sample/detection reagent mixture.

8. The system of claim 1, wherein the colloidal particles further comprises a population of particles to whose surfaces are attached one member of a second chemical binding pair, wherein the substance contains second members of both the first and the second chemical binding pairs, and wherein the extinction changes at the predefined wavelength are representative of the presence of the substance.

9. The system of claim 1, wherein the spectrophotometric detection means further comprises means to measure optical extinction at a second predefined wavelength, and wherein an extinction change at one wavelength is proportional to the number of single colloidal particles in the sample/detection reagent mixture and an extinction change at the other wavelength is proportional to the number of doublet colloidal particles in the sample/detection reagent mixture.

10. The system of claim 1, wherein the chemical binding pair is selected from the group consisting of antibody-antigen, receptor-ligand, polynucleotide-complementary polynucleotide, and lectin-carbohydrate.

11. The system of claim 1, wherein the diameter of the colloidal particles is between 10 and 100 nanometers.

12. A method of determining the presence of a member of a chemical binding pair in an aqueous sample comprising the steps of:

selecting a material which is chemically stable in aqueous solution and which has a complex refractive index n–ik wherein a real part n of the index approaches zero when an imaginary part k approaches $\sqrt{2}$, thereby yielding a resonant optical extinction in a wavelength region where water is optically transparent;

producing an aqueous solution of colloidal particles of the material, the colloidal particles being spherical single particles with diameters less than a wavelength of visible light;

attaching first members of a first chemical binding pair to the surfaces of the colloidal particles;

adding an aqueous sample to be analyzed to the colloidal particles having said attached chemical binding member, and mixing thoroughly; and measuring a resonant wavelength of the colloidal particles without any bound-free separation step, an extinction change at the resonant wavelength being indicative of changes in particle-particle association which is related to the presence and amount, in the sample, of a substance bearing a second member of the first chemical binding pair.

13. The method of claim 12, wherein the attaching step further comprises attaching first members of a second chemical binding pair to a separate population of the colloidal particles and mixing said separate population with the colloidal particles having the attached chemical binding member of the first chemical binding pair, wherein the substance bears second members of both the first and the second chemical binding pairs, and wherein the extinction change at the resonant wavelength is due to changes in particle-particle association and is representative of the presence of the substance.

14. The method of claim 12, wherein said material is a semiconductor quantum well material and said particles are quantum dots.

15. The method of claim 12, wherein the selected material is a metal.

16. The method of claim 15, wherein the metal is selected from the group consisting of silver and gold coated with silver.

17. A method of determining the presence of an inhibitor of a chemical binding interaction, the method comprising the steps of:

selecting a material which is chemically stable in aqueous solution and which has a complex refractive index n–ik wherein a real part n of the index approaches zero when an imaginary part k approaches $\sqrt{2}$, thereby yielding a resonant optical extinction in a wavelength region where water is optically transparent;

producing an aqueous solution of colloidal particles of the material, the colloidal particles being spherical single particles with diameters less than a wavelength of visible light;

attaching a first member of a chemical binding pair to the surfaces of the colloidal particles in a first aliquot;

attaching a second member of a chemical binding pair to the surfaces of the colloidal particles in a second aliquot;

combining the two aliquots so that the binding interaction leads to particle-particle association;

adding as a sample a chemical compound with unknown activity as an inhibitor of the binding interaction; and measuring a resonant wavelength of the colloidal particles without any bound-free separation step, an extinction change at the resonant wavelength being related to the presence and activity, in the sample, of an inhibitor of the binding interaction.

18. The method of claim 17, wherein said material is a semiconductor quantum well material and said particles are quantum.

19. The method of claim 17, wherein the selected material is a metal.

20. The method of claim 19, wherein the metal is selected from the group consisting of silver and gold coated with silver.

21. A method of assaying the presence of a specific polynucleotide sequence, the method comprising the steps of:

selecting a material which is chemically stable in aqueous solution and which has a complex refractive index n–ik wherein a real part n of the index approaches zero when an imaginary part k approaches $\sqrt{2}$, thereby yielding a resonant optical extinction in a wavelength region where water is optically transparent;

producing an aqueous solution of colloidal particles of the material, the colloidal particles being spherical single particles with diameters less than a wavelength of visible light;

attaching first polynucleotide sequences complementary to one region of said specific polynucleotide sequence to the surfaces of the colloidal particles in a first aliquot;

attaching second polynucleotide sequences complementary to a different region of said specific polynucleotide sequence to the surfaces of the colloidal particles in a second aliquot;

combining the two aliquots with an aqueous sample to be analyzed for said specific polynucleotide sequence so that the binding interaction between said specific polynucleotide sequence and the complementary regions on the first and second polynucleotide sequences leads to particle-particle association; and measuring a resonant wavelength of the colloidal particles without any bound-free separation step, an extinction change at the resonant wavelength being related to the presence, in the sample, of said specific polynucleotide sequence.

22. The method of claim 21, wherein said material is a semiconductor quantum well material and said particles are quantum dots.

23. The method of claim 21, wherein the selected material is a metal.

24. The method of claim 23, wherein the metal is selected from the group consisting of silver and gold coated with silver.

* * * * *